United States Patent [19]
Moyet-Ortiz

[11] Patent Number: 5,267,989
[45] Date of Patent: Dec. 7, 1993

[54] URINE COLLECTION DEVICE

[76] Inventor: Francisco Moyet-Ortiz, Valle Tolimas, Calle 11 N-17, Caguas, P.R. 00624

[21] Appl. No.: 949,145
[22] Filed: Sep. 23, 1992
[51] Int. Cl.⁵ .............................................. A61F 5/44
[52] U.S. Cl. .................................. 604/349; 604/323; 128/760; 4/144.1
[58] Field of Search ................................. 604/349–352, 604/323; 128/760; 4/144.1–144.3

[56] References Cited

U.S. PATENT DOCUMENTS

| | | | |
|---|---|---|---|
| 2,976,869 | 3/1961 | Silverstone et al. | 604/350 |
| 4,559,049 | 12/1985 | Haan | 604/350 |
| 4,938,748 | 7/1990 | Yum et al. | 604/323 |
| 5,032,118 | 7/1991 | Mason | 604/349 |
| 5,065,459 | 11/1991 | Tjahaja et al. | 4/144.2 |

FOREIGN PATENT DOCUMENTS

| | | | |
|---|---|---|---|
| 2188545 | 10/1987 | United Kingdom | 4/144.1 |
| 2243594 | 6/1991 | United Kingdom | 4/144.2 |

Primary Examiner—David Isabella
Assistant Examiner—Rob Clarke
Attorney, Agent, or Firm—William Nitkin

[57] ABSTRACT

A urine collection device for use by an incontinent male made of an envelope having a front sheet and a rear sheet sealed together along side edges with an absorbent pad positioned on the inner side of the rear sheet. The top of the envelope is held together by a resealable contact adhesive and is openable for insertion of the user's penis. The bottom of the envelope includes a drain with a tube running to a urine storage bag.

9 Claims, 2 Drawing Sheets

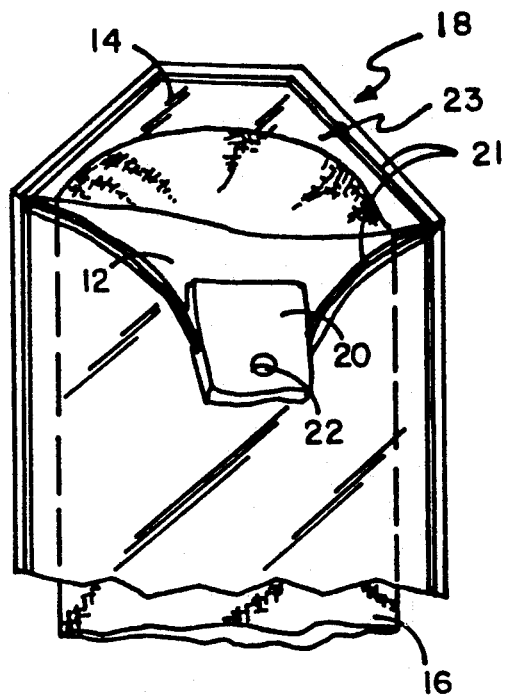
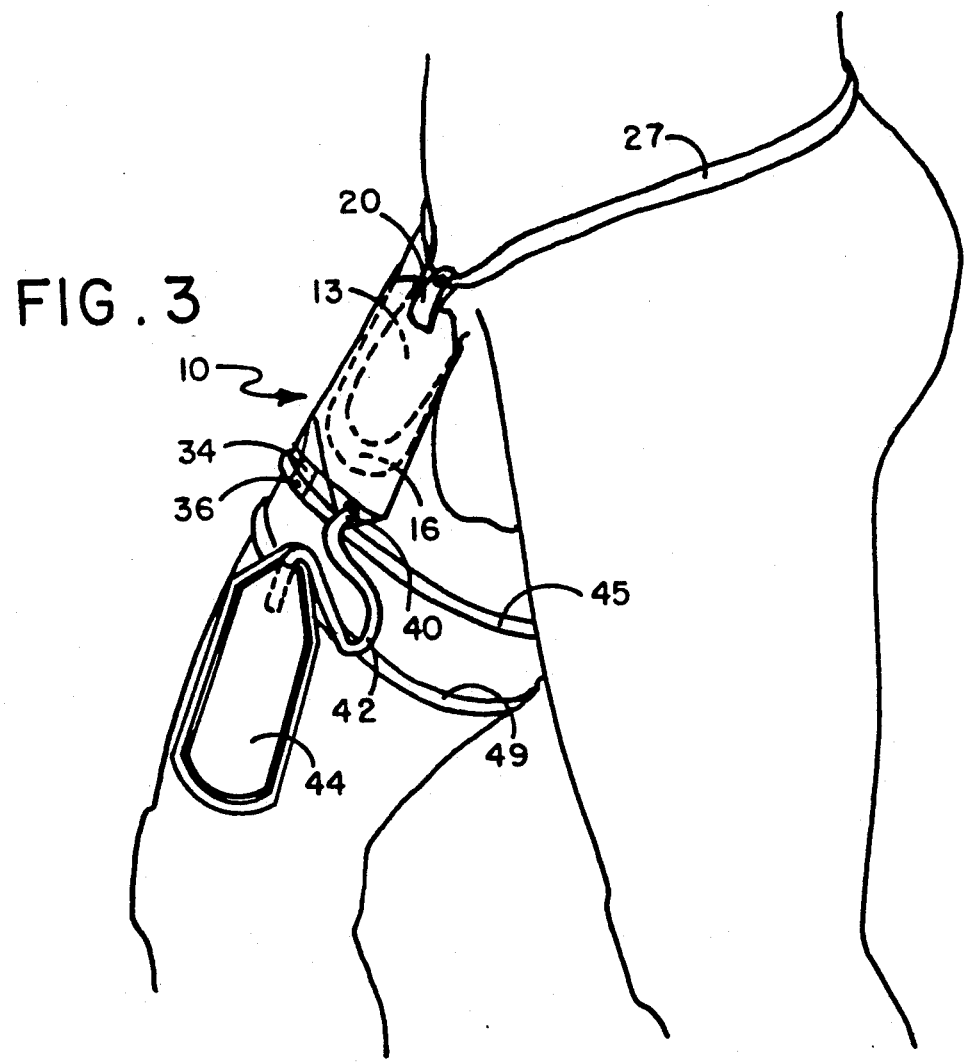
FIG. 2
FIG. 3

URINE COLLECTION DEVICE

BACKGROUND OF THE INVENTION

1. Field of the Invention

The device of this invention resides in the area of urine collectors and more particularly relates to a device worn by an incontinent male for the collection of any passed urine.

2. Description of the Prior Art

Incontinent males who pass urine during the day while wearing clothing will often display a wet spot in the crotch of their pants. The leaked urine can cause discomfort, irritation and embarrassment. In some cases these individuals wear adult-size diapers for the collection of such urine and for the prevention of leakage through to the crotch area of the pants. Such diapers retain urine against the penis and other parts of the lower torso of the incontinent male which urine then can cause significant skin irritation. Moreover, adult-size diapers can be uncomfortable to wear as they become bulky as they retain urine in their absorbent padding around the pelvic area. Many of these diapers spread urine around the gluteal area of the wearer as urine is absorbed by the padding of the diaper. This urine contact with the body can cause the formation of skin ulcers which can be a serious problem especially for bed-ridden individuals or those sitting for long periods of time. High humidity can exacerbate the problems of skin irritation for those adults wearing padded diapers.

SUMMARY OF THE INVENTION

It is an object of this invention to provide a new, disposable, hygienic urine collection device which is more comfortable for incontinent males to utilize.

The device of this invention includes a plastic envelope-like member which is attached to a urine storage bag. The envelope-like member has a front and a rear plastic sheet which are joined together along their side edges by heat-sealing or equivalent means. An absorbent pad is positioned on the rear sheet. When the device is to be utilized, the top of the envelope is opened and the user's penis is inserted into the envelope. The envelope is held in place by a cord passing through an aperture in a tab extending from the top of the front sheet. The cord is tied around the user's waist to hold the device in position. Because large amounts of urine can be passed, the cord must be sufficiently strong and securely tied to the user's body to hold the weight of such urine while drainage occurs through a tube into the storage bag. The absorbent pad on the rear sheet of the envelope traps and retains any dribbled urine to draw it away from the penis to help prevent rashes or bacterial infections to the penis. Chemicals such as antibiotics and bactericides can be added to the pad to help aid in the pad's antiseptic function. Deodorants to prevent odors can also be added to the pad. These chemicals can be of the type activated by moisture and can, in some embodiments, be incorporated into the pad in powder form which when contacted by moisture of the urine, or even from sweat, will become activated. Other types of chemicals, such as currently used in disposable diapers, for example fluid-absorbent gels, also could aid in performing the antibiotic, deodorizing and bactericidal functions of the chemicals used in the pad. Padding of the type which draws moisture away from the surface of the padding can also be incorporated into the device of this invention.

The urine collection device of this invention can be easily carried and disposed of on a regular basis. The flat, small size of the device will enable the user to carry several folded devices conveniently in his pocket.

BRIEF DESCRIPTION OF THE DRAWINGS

FIG. 2 illustrates a front view of the top of the envelope opened for use.

FIG. 3 illustrates a perspective view of the device in its use mode.

DESCRIPTION OF THE PREFERRED EMBODIMENT(S)

Figure 1:
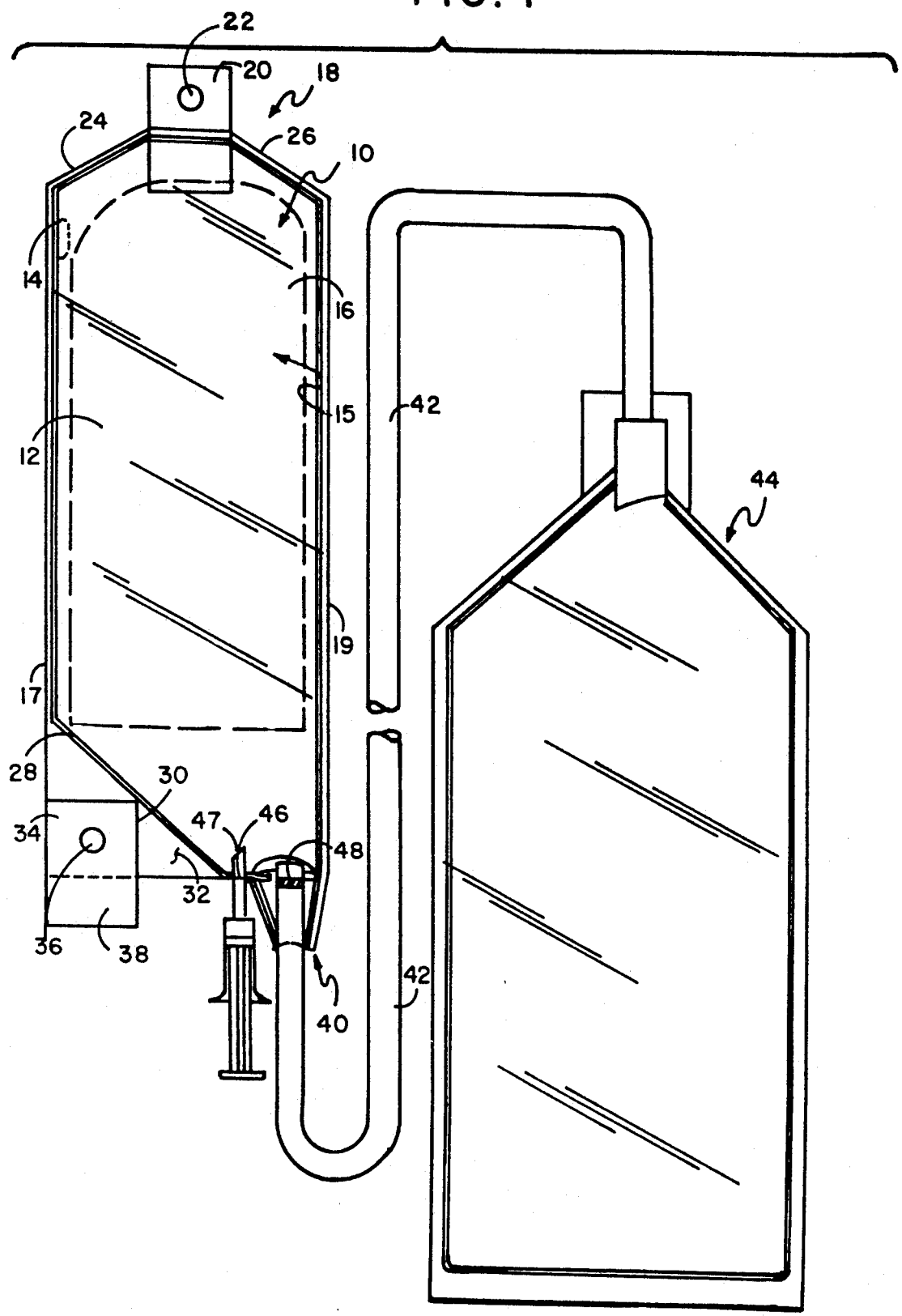
FIG. 1 illustrates a front view of the urine collection device of this invention in its collapsed, non-use mode.

FIG. 1 illustrates a front view of the urine collection device 10 of this invention. Front sheet 12, in a preferred embodiment, is heat-sealed around its first and second side edges 17 and 19, respectively, to rear sheet 14, forming an envelope 15. On the inside of rear sheet 14 is adhered absorbent padding 16. At top 18 of envelope 15 is tab 20 positioned on the exterior of front sheet 12 and having aperture 22 defined in its portion extending above top 18. Envelope 15, in a preferred embodiment, is generally rectangular and is approximately 7.5 inches long and 2.5 inches wide when flat. Top 18 has first angled side 24 and second angled side 26 extending up to tab 20. Front sheet 12 and rear sheet 14 are held together across top 18 under tab 20 by resealable contact adhesive 21, as seen in FIG. 2, so that when front sheet 12 and rear sheet 14 are pulled apart, they can be readhered to one another by recontacting them and pressing them together. At the bottom of envelope 15 can be seen heat-sealed seam 28 which runs at an angle from the left first side 17 down to bottom 30 of the envelope. The portions of front sheet 12 and rear sheet 14 to the left of seam 28 can, in one embodiment, be bonded together, forming triangular attachment area 32 on which is positioned second tab 34 with second aperture 36 defined therein. A self-adhesive tab extension 38 can, in one embodiment, protrude from second tab 34. Lower cord 45, seen in FIG. 3, passes through second aperture 36 to be tied around the user's leg to hold the bottom of the envelope against the user's leg. If desired, in an alternate embodiment, the adhesive on self-adhesive tab extension 38 can be exposed by removing a paper covering, not shown, on the rear of second tab 34 which adhesive surface can be placed against the user's leg to help hold the bottom of envelope 15 in position against the user's leg. At the right corner of bottom 30 of envelope 15 is drain opening 40 which leads to drain tube 42 which extends to urine collection and storage bag 44 which can be attached by storage bag cord 49 or equivalent means to the user's leg as seen in FIG. 3. The storage bag is positioned below the envelope so that the urine is drained by gravity into the storage bag. Drain opening 40 can contain a one-way valve 48 to prevent any back-up of urine from storage bag 44.

Envelope 15 can be opened by peeling open and separating front and rear sheets 12 and 14, respectively, to expose open top 23, as seen in FIG. 2, into which the user's penis 13 is inserted. Once penis 13 is inserted into the envelope, the sides of top 18 are resealed against one another to form a seal around the upper portion of the penis. The device of this invention is designed to be maintained in a sterile condition until opened and used.

Top cord 27 is passed through aperture 22 and is tied around the user's waist. In some embodiments resealable chemical insertion opening 46 at bottom 30 can be provided for the injection of selected chemicals into the envelope which chemicals can be medicines helpful, for example, in preventing infections or for preventing odor as discussed above. The device of this invention can also be used for the collection of urine for laboratory testing purposes.

Although the present invention has been described with reference to particular embodiments, it will be apparent to those skilled in the art that variations and modifications can be substituted therefor without departing from the principles and spirit of the invention.

I claim:

1. A urine collection device for use by an incontinent male, comprising:
   a envelope structure being generally planar and rectangular in shape having a top portion, bottom portion, left side and right side, said structure having a front sheet and a rear sheet, said sheets each having an inner and an outer surface;
   an absorbent pad positioned and adhered to the inner surface of said rear sheet, said front and rear sheets being sealed together along said sides beyond the positioning of said pad;
   contact adhesive applied at the top portions of the inner surfaces of said front and rear sheets, said contact adhesive releasably holding the top portions of said front and rear sheets together in the device's pre-use mode and allowing separation of the tops of said front and rear sheets for the insertion of the male's penis into said envelope with said top portions of said front and rear sheets to be resealed around said penis in the device's use mode;
   means to retain said envelope on said penis; and
   means to collect urine passed into said envelope.

2. The device of claim 1 wherein said front sheet and rear sheet are sealed together from said left side near the bottom of said envelope at an angle extending to the bottom, said sealed area defining a left sealed triangular area of said envelope and a right unsealed bottom portion of said envelope; and
   a first tab member adhered to said left sealed triangular area, said first tab adapted to be held against said user's leg.

3. The device of claim 2 wherein said means to retain said envelope on said penis comprises a second tab having an aperture defined therein, said second tab adhered to the top outer surface of said front sheet, said second tab adapted to have a cord pass therethrough to be tied to the user's body.

4. The device of claim 3 wherein said first tab member has an aperture defined therein adapted for receipt of a cord to tie the bottom of said envelope to the user's leg.

5. The device of claim 3 wherein said first tab member has a self-adhesive portion adapted to adhere to the user's leg.

6. The device of claim 3 further including:
   a drain defined in said right unsealed bottom portion of said envelope;
   a tube member having a first and second end, the first end of said tube member attached to said drain of said envelope;
   a urine storage bag having an opening defined in the top thereof, said opening receiving the second end of said tube member to direct urine from the bottom of said envelope to said storage bag; and
   means to attach said storage bag to the user's leg below said envelope.

7. The device of claim 6 further including a one-way valve disposed in said tube to prevent any back-up of urine from said storage bag to said envelope.

8. The device of claim 7 further including chemical additives placed within said envelope for antibiotic, bactericidal, medicinal and deoderizing purposes.

9. The device of claim 8 further including a resealable inlet aperture defined in said envelope through which can be introduced selected chemical additives into said envelope.

* * * * *